United States Patent
Raposo et al.

(10) Patent No.: US 10,603,265 B2
(45) Date of Patent: Mar. 31, 2020

(54) SKIN WHITENING PEPTIDE AGENTS

(71) Applicants: INSTITUT CURIE, Paris (FR); CENTRE NATIONAL DE LA RECHERCHE SCIENTIFIQUE, Paris (FR)

(72) Inventors: Graca Raposo, Paris (FR); Cecile Campagne, New York, NY (US); Cedric Delevoye, Charenton le Pont (FR)

(73) Assignees: INSTITUT CURIE, Paris; CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/506,281

(22) PCT Filed: Aug. 31, 2015

(86) PCT No.: PCT/EP2015/069862
§ 371 (c)(1),
(2) Date: Feb. 24, 2017

(87) PCT Pub. No.: WO2016/034541
PCT Pub. Date: Mar. 10, 2016

(65) Prior Publication Data
US 2017/0246098 A1    Aug. 31, 2017

(30) Foreign Application Priority Data
Sep. 1, 2014  (EP) .................................. 14306344

(51) Int. Cl.
| A61K 8/64 | (2006.01) |
| A61Q 19/02 | (2006.01) |
| A61K 8/06 | (2006.01) |
| A61K 8/14 | (2006.01) |

(52) U.S. Cl.
CPC .................. *A61K 8/64* (2013.01); *A61K 8/06* (2013.01); *A61K 8/14* (2013.01); *A61Q 19/02* (2013.01)

(58) Field of Classification Search
None
See application file for complete search history.

(56) References Cited

U.S. PATENT DOCUMENTS

| 8,669,348 | B2 | 3/2014 | Raposo et al. |
| 9,456,972 | B2 * | 10/2016 | Choi .................. A61K 8/64 |
| 2004/0171554 | A1 | 9/2004 | Deshayes et al. |
| 2008/0152600 | A1 | 6/2008 | Huang et al. |
| 2008/0227716 | A1 | 9/2008 | Rothe et al. |
| 2012/0321575 | A1 | 12/2012 | Raposo et al. |

FOREIGN PATENT DOCUMENTS

| DE | 10355743 | * 11/2003 |
| DE | 103 55 743 | 7/2005 |
| JP | H07188282 | 7/1995 |
| WO | WO 2009/010356 | 1/2009 |
| WO | WO2009010356 | * 1/2009 |
| WO | WO 2009/141541 | 11/2009 |
| WO | WO 2010/111753 | 10/2010 |
| WO | WO 2011/047868 | 4/2011 |
| WO | WO 2013/064583 | 5/2013 |
| WO | WO2014086785 | * 6/2014 |

OTHER PUBLICATIONS

Goodwin et al. ("Peptides as Therapeutics with Enhanced Bioactivity"; Current Medicinal Chemistry, 2012,19, 4451-4461).*
Eucerin (<https://www.google.com/search?q=age+spots+AND+HYPERPIGMENTATION&rlz=1C1GCEB_enUS773US774&source=Int&tbs=cdr%3A1%2Ccd_min%3A%2Ccd_max%3A2015&tbm=> available online Feb. 20, 2014).*
Written Opinion in International Application No. PCT/EP2015/069862, dated Jan. 26, 2016, pp. 1-12.

* cited by examiner

*Primary Examiner* — James H Alstrum-Acevedo
*Assistant Examiner* — Tara L Martinez
(74) *Attorney, Agent, or Firm* — Saliwanchik, Lloyd & Eisenschenk (57) ABSTRACT

The present invention provides new peptides useful as skin whitening agents and their uses in cosmetic or therapeutic applications.

10 Claims, 5 Drawing Sheets
Specification includes a Sequence Listing.

SKIN WHITENING PEPTIDE AGENTS

CROSS-REFERENCE TO RELATED APPLICATION

This application is the U.S. national stage application of International Patent Application No. PCT/EP2015/069862, filed Aug. 31, 2015.

The Sequence Listing for this application is labeled "Seq-List.txt" which was created on Aug. 28, 2015 and is 4 KB. The entire content of the sequence listing is incorporated herein by reference in its entirety.

FIELD OF THE INVENTION

The present invention relates to the field of cosmetics and medicine, in particular of dermatology. It provides new peptides that reduce the synthesis of melanic pigments in melanocytes and are thus useful as whitening agents.

BACKGROUND OF THE INVENTION

Pigmentation results from the synthesis and distribution of melanic pigments most notably in the skin, the hair and the pigmentary epithelium of the iris. Thus, the color of the skin, the hair and the eyes depends principally on the types of pigments present and their concentrations.

Melanins are macromolecules produced in melanosomes, i.e. specialized intracellular organelles contained in melanocytes, by the addition or condensation of monomers formed from tyrosine (eumelanin) or of tyrosine and cysteine (pheomelanin). The mechanism by which melanins are synthesized, or melanogenesis, is particularly complex and involves various enzymes, principally tyrosinase and the tyrosine related protein (tyrosinase-related protein-1 or Tyrp-1).

Melanosome maturation can be broken down into four stages on the basis of morphological criteria. Stage I corresponds to a compartment delimited by a membrane with a variable quantity of intraluminal membranes. Stage II is an ellipsoidal structure with characteristic protein-like striations. Melanin is detected from stage III by electron-dense deposits along the striations. Stage IV is an electron-dense structure in which the internal striations are no longer visible and corresponding to the mature melanosome ready to be transferred to the keratinocytes (Van Den Bossche et al., 2006, Traffic, 7, 769-778; Raposo and Marks, Nat Rev Mol Cell Biol. October 2007; 8(10): 786-797).

During the process of biogenesis, stage III and IV melanosomes are obtained by the transfer of enzymes that are key to melanin synthesis in the pre-melanosomes (Raposo et al., 2001, J. Cell Biol. 152, 809-824). This type of transfer requires in particular the participation of three adaptor protein (AP) complexes, named AP-1 to AP-3, which are heterotetramers having the role of recruiting enzymes in the transport vesicles.

Although the melanin in the skin represents suitable protection against UV radiation, darker or overpigmented skin such as hyperpigmentation (e.g. chloasma or melasma), freckles (ephelides), age spots (lentigines), sun spots or seborrheic keratosis, may result in serious aesthetic problems. These pigment spots may be induced by melanocyte dysfunction or may be due to an accident, e.g. by photosensitization or post-lesion scarring. The sun very frequently plays an important role and prevention can be achieved, in particular, by regular sun protection with a high light protection factor.

In order to remove unattractive pigment spots, various possibilities are available, such as lasers, dermabrasion or other electrosurgical methods and bleaching creams comprising depigmentation or whitening substances. The latter alternative has the advantage that it is significantly less expensive and more pleasant for the patient.

A whitening molecule acts on skin melanocytes and interferes with one or more stages of melanogenesis. Known depigmentation substances are in particular hydroquinone and its derivatives, ascorbic acid and its derivatives, placental extracts, kojic acid, niacinamide, vitamin C, rucinol, arbutin, plants extracts such as from *Morus alba* or *Phyllanthus emblica*, iminophenols (WO 99/22707), the combination of carnitine and quinone (DE 19806947), aminophenol amide derivatives (FR 2772607) or benzothiazole derivatives (WO 99/24035). However, these substances present various disadvantages such as low efficiency, instability of the formulations, short shelf life, nonspecific action, or toxic, irritating or allergenic properties.

In the last few years, new approaches to whiten skin have appeared using antisense oligonucleotides or peptide inhibitors. For example, it was envisaged to treat hyperpigmentation with antisense oligonucleotides regulating the expression of tyrosinase (FR 2804960), peptides inhibiting the interaction between the AP-2 or AP-3 complex and the tyrosinase (WO 2009/010356) or directly inhibiting the tyrosinase (WO 2009/003034).

It was known that a kinesin, named KIF13A, was able to interact with a sub-unit of AP-1 (Nakagawa et al., Cell, 2000, vol. 103, 569-581) and the inventors previously showed that the synthesis of melanic pigments could be efficiently decreased with a nucleic acid inhibiting the expression of a sub-unit of AP-1 adaptor complex which interacts with kinesin KIF13A (WO 2009/141541). This nucleic acid was not only able to disrupt the transport of melanogenesis enzymes of the endosomes toward the pre-melanosomes, thus blocking the maturation of these organelles, but also was able to decrease the expression of melanogenesis enzymes. It thus constitutes an effective depigmentation agent. However, stability, formulation and route of administration remain tricky when using nucleic acid as dermatological or cosmetic agent.

Thus, there is still a need for novel skin whitening agents that are able to disrupt the transport of melanogenesis enzymes in the pre-melanosomes and thus have a high effectiveness, but also good formulation properties.

SUMMARY OF THE INVENTION

The aim of the present invention is to provide novel skin whitening peptide agents that are non-toxic and have a specific action on melanogenesis through the inhibition of the interaction between a subunit of the AP-1 adaptor complex and the kinesin KIF13A.

In a first aspect, the present invention relates to a skin whitening peptide having from 3 to 15 amino acids in length and comprising a sequence of at least three successive amino acids of the amino acid sequence of SEQ ID NO: 1, a functional derivative or a physiologically acceptable salt thereof.

The peptide may comprises an amino acid sequence selected from the group consisting of the amino acid sequences EPL, PLN, LNN, NNL, NLQ, LQV, QVA, VAV, AVK, and SEQ ID NO: 1 to 16.

Preferably, the peptide has from 3 to 11 amino acids in length, more preferably from 3 to 7 amino acids in length.

The peptide may consist of an amino acid sequence selected from the group consisting of the amino acid sequences of (i) the amino acid sequences EPL, PLN, LNN, NNL, NLQ, LQV, QVA, VAV, AVK, and SEQ ID NO: 1 to 16, and (ii) any sequence comprising 6, 7, 8, 9, or 10 successive amino acids of the amino acid sequence of SEQ ID NO: 1.

In particular, the peptide may comprise, or consist of, an amino acid sequence selected from the group consisting of the amino acid sequences AVK, VAVK (SEQ ID NO:9) and QVAVK (SEQ ID NO: 16). Preferably, the peptide comprises, or consists of, the amino acid sequence QVAVK (SEQ ID NO: 16).

In another aspect, the present invention relates to a nucleic acid coding for a peptide according to the invention, an expression cassette comprising said nucleic acid, an expression vector comprising said nucleic acid or said expression cassette, and a host cell comprising said nucleic acid, expression cassette or expression vector.

In another aspect, the present invention relates to a cosmetic or pharmaceutical composition comprising a peptide according to the invention, a functional derivative or a physiologically acceptable salt thereof, and a physiologically acceptable carrier and/or excipient.

In said composition, the peptide may be contained in liposomes. The composition may further comprise one or several other active substances. Preferably, said composition is adapted for administration by topical route.

In a further aspect, the present invention relates to a peptide according to the invention, as medicament.

The present invention also relates to a peptide according to the invention, a functional derivative or a physiologically acceptable salt thereof, for use in the prevention or treatment of hyperpigmentation. It further relates to a method for treating hyperpigmentation comprising administering a therapeutically effective dose of a peptide according to the invention to a subject in need thereof. The invention also relates to a use of a peptide of the invention for manufacturing a medicament for the treatment or the prevention of hyperpigmentation.

In particular, hyperpigmentation may be selected from the group consisting of melasma such as idiopathic melasma (i.e. melasma not associated with pregnancy nor ingestion of oral contraceptives) or chloasma (also named mask of pregnancy), actinic lentigo, pigmentary after-effects from acne, pigmentations due to photosensitization, post-inflammatory pigmentations due to an abrasion, a burn, a scar, dermatosis and/or contact allergy, meadows dermatitis, pigmentations due to poison ivy, freckles, and nevi such as congenital giant nevus, Becker nevus or Spitz nevus.

In another aspect, the present invention relates to the use of a peptide according to the invention, a functional derivative or a physiologically acceptable salt thereof, as cosmetic agent, in particular as skin whitening, depigmenting or lightening cosmetic agent.

The present invention further relates to a cosmetic method for whitening, depigmenting or lightening human skin, comprising topically applying onto human skin a cosmetic composition of the invention.

BRIEF DESCRIPTION OF THE DRAWINGS

FIG. 5: MNT1 melanocytes were seeded on glass coverslips and cultured 3 days with 10 μM of QK-5 peptide (SEQ ID NO: 16) or $H_2O$ as a control. Cells were fixed in cold methanol and co-stained using a rabbit anti-human KIF13A and a mouse anti-human γ-adaptin as primary antibodies and goat anti-rabbit or mouse coupled to Alexa-488 or 546 (Molecular Probes). Coverslips were mounted in Dabco (Invitrogen) medium and images were acquired on an Eclipse 80i Upright Microscope (Nikon) and deconvoluted. Images are maximum-intensity z projections of up to 15 3D image stacks acquired using ImageJ software. Analysis was performed by quantifying the intensity of overlapping KIF13A and AP-1 pixels and by normalizing them to the control. QK-5 peptide incubation on melanocytes decreased about 84±7% the co-localization of KIF13A with AP-1. Data are presented as mean±standard deviation. ***; p value (two tailed)<0.001.

DETAILED DESCRIPTION OF THE INVENTION

The inventors previously showed that AP-1 adaptor complex and kinesin KIF13A are essential for the synthesis of the melanin pigment in skin melanocytes (WO 2009/141541). Both proteins interact, and this interaction is critical for maintenance of the pigmented phenotype.

As illustrated in the experimental section, they designed and tested small peptides of the β1-adaptin subunit of the AP-1 complex (from 3 to 11 amino acids) for their ability to disrupt the AP-1/KIF13A interaction. They developed a biochemical assay in which cell lysates were incubated with peptides. AP-1 was immunoprecipitated from the cell lysates and immunoprecipitates were loaded on gels for western blot analysis by revealing its partner, KIF13A. Using this assay, they observed that the 11-amino acid EK peptide (SEQ ID NO: 1) and fragments thereof, in particular the 5 amino acid peptide QVAVK (SEQ ID NO: 16), efficiently decreased the AP-1/KIF13A interaction in skin melanocytes.

These results were confirmed by (i) incubation of these peptides on live skin melanocytic cells and measurement of the production of pigment after 3 days of incubation, (ii) immunofluorescence showing that colocalization of AP-1 with KIF13A is decreased after the incubation of the peptides on cells, (iii) electron microscopy showing a significant reduction in the number of fully mature pigmented melanosomes, and (iv) incubation of these peptides on synthetic 3D human reconstructed pigmented epidermis showing a significant decrease of melanin content and none cytotoxic effect of the peptides observed at the ultrastructural level.

The inventors thus herein demonstrated that identified peptides are able to block the interaction between the AP-1 adaptor complex and KIF13A, to decrease the production of melanin in melanocytes and to delay the formation of fully mature pigmented melanosomes in epidermal melanocytes. Surprisingly, peptides as small as 3 amino acids result in a decrease of about 20% of the intracellular melanin content in synthetic human skin epidermis.

One of the major advantages of such small peptides is that they can diffuse freely across cell membrane and can thus be easily used as whitening agents for dermatology and/or cosmetology purposes.

DEFINITIONS

As used herein, the terms "peptide", "oligopeptide" are "polypeptide" are employed interchangeably and refer to a chain of amino acids linked by peptide bonds, regardless of the number of amino acids forming said chain. The peptide may comprise residues from any of the naturally occurring amino acids and/or from any non-naturally occurring amino acids. In the peptide sequences described herein, the amino acids are represented by their one-letter code according to the following nomenclature: C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan and Y: tyrosine. The amino acids constituting the peptide of the invention may be in the L or D configuration, preferably the L configuration. The peptide according to the invention may comprise one or more amino acids which are rare, synthetic or chemically modified amino acids in particular acetylated amino acids (e.g. N-acetyl-L-alanine), amidated amino acids (e.g. L-alanine amide), formylated amino acids (e.g. N-formyl-L-methionine), hydroxylated amino acids (e.g. hydroxyproline, hydroxylysine, allohydroxylysine), lipid conjugated amino acids (e.g. N6-myristoyl-L-lysine), ethylated or methylated amino acids (e.g. N-methyl-L-alanine, 6-N-methylysine, N-ethylglycine, N-methylglycine, N-ethylasparagine, allo-isoleucine, N-methylisoleucine, N-methylvaline), phosphorylated amino acids (e.g. N6-phospho-L-lysine) or any other rare, synthetic or chemically modified amino acids known by the skilled person such as, for example, ornithine, norleucine, norvaline, β-alanine, phenylglycine, homoarginine and cyclohexyl-alanine.

The peptide molecule according to the present invention may further comprise an element facilitating the penetration of the molecule into the cell. In particular, this element is a peptide facilitating the cell penetration of the molecule (CPP: cell-penetrating peptide element). These peptides are well known to one skilled in the art (for example, Vivès et al., Biochimic & Biophysica Acta, 2008, 1786, 126-138). For example and not by way of limitation, the peptide facilitating cell penetration can be chosen from the group consisting of a Tat peptide, an antennapedia or penetratin peptide, and a peptide rich in arginine and/or lysine, in particular a poly-arginine.

The term "AP-1" used in this document refers to AP-1 adaptor complex which acts in the trans-Golgi and endocytic network. It should not be confused with the transcription factor of the same name which consists of proteins coded by genes that are members of the jun and fos families. AP-1 adaptor complex is composed of 4 sub-units, γ, β1, σ1 and µ1. The GeneID accession numbers for the γ, β1, σ1 and µ1 sub-units of AP-1 are, respectively, GeneID164, GeneID162, GeneID1174 and GeneID8907.

The term "KIF13A", "kinesin-like protein KIF13A" or "kinesin KIF13A" refers to a plus end-directed microtubule-dependent motor protein involved in intracellular transport and regulating various processes such as mannose-6-phosphate receptor (M6PR) transport to the plasma membrane, endosomal sorting during melanosome biogenesis, recycling endosome biogenesis and cytokinesis. The GeneID accession number for human kinesin Kif13A is GeneID63971. The Uniprot accession number is Q9H1H9.

The terms "melanin," "melanins", "melanic pigments" and "pigments" are used interchangeably herein. They include the various pigments likely to be synthesized in melanosomes, including eumelanin or pheomelanin.

As used herein, the term "about" refers to a range of values±10% of the specified value. For example, "about 20" includes ±10% of 20, or from 18 to 22. Preferably, the term "about" refers to a range of values±5% of the specified value.

In a first aspect, the present invention relates to an isolated skin whitening peptide having from 3 to 15 amino acids in length and comprising a sequence of at least three successive amino acids of the EPLNNLQVAVK (SEQ ID NO: 1) peptide, a functional derivative or a physiologically acceptable salt thereof.

In the experimental section, the inventors showed that several 3 amino acid peptides spanning the EPLNNLQVAVK sequence, are able to efficiently decrease the pigmentation of skin melanocytes as well as synthetic epidermis.

Thus, in an embodiment, the peptide comprises, consists of, or essentially consists of,
a sequence of three successive amino acids of the EPLNNLQVAVK sequence, i.e. an amino acid sequence selected from the group consisting of the amino acid sequences EPL, PLN, LNN, NNL, NLQ, LQV, QVA, VAV and AVK;
a sequence of four successive amino acids of the EPLNNLQVAVK sequence, i.e. an amino acid sequence selected from the group consisting of the amino acid sequences EPLN (SEQ ID NO: 2), PLNN (SEQ ID NO: 3), LNNL (SEQ ID NO: 4), NNLQ (SEQ ID NO: 5), NLQV (SEQ ID NO: 6), LQVA (SEQ ID NO: 7), QVAV (SEQ ID NO: 8) and VAVK (SEQ ID NO: 9); or
a sequence of five successive amino acids of the EPLNNLQVAVK sequence, i.e. an amino acid sequence selected from the group consisting of the amino acid sequences EPLNN (SEQ ID NO: 10), PLNNL (SEQ ID NO: 11), LNNLQ (SEQ ID NO: 12), NNLQV (SEQ ID NO: 13), NLQVA (SEQ ID NO: 14), LQVAV (SEQ ID NO: 15) and QVAVK (SEQ ID NO: 16).

In another embodiment, the peptide comprises, consists of, or essentially consists of, any sequence comprising 6, 7, 8, 9, or 10 successive amino acids of the amino acid sequence of SEQ ID NO: 1. In a further embodiment, the peptide comprises, consists of, or essentially consists of, the amino acid sequence of SEQ ID NO: 1.

In a particular embodiment, the peptide of the invention comprises, consists of, or essentially consists of, an amino acid sequence selected from the group consisting of the amino acid sequences EPL, PLN, LNN, QVA, VAV, AVK, LQVA (SEQ ID NO: 7), QVAV (SEQ ID NO: 8), VAVK (SEQ ID NO:9) and QVAVK (SEQ ID NO: 16). Preferably, the peptide comprises, consists of, or essentially consists of, an amino acid sequence selected from the group consisting of the amino acid sequences EPL, LNN, QVA, AVK, VAVK (SEQ ID NO:9) and QVAVK (SEQ ID NO: 16).

In a preferred embodiment, the peptide of the invention comprises, consists of, or essentially consists of, an amino acid sequence selected from the group consisting of the amino acid sequences AVK, VAVK (SEQ ID NO:9) and QVAVK (SEQ ID NO: 16). Preferably, the peptide comprises, consists of, or essentially consists of, an amino acid sequence selected from the group consisting of the amino acid sequences AVK and QVAVK (SEQ ID NO: 16). More preferably, the peptide comprises, consists of, or essentially consists of, the amino acid sequence QVAVK (SEQ ID NO: 16).

As used herein, the term "essentially consists of" means that at most two substitutions or one deletion or addition are permitted, i.e. that the amino acid sequence of the peptide may have one or two amino acid difference from the specified sequence. Preferably, this term means that the peptide has an amino acid sequence having at least 90%, more preferably at least 95%, identity to the specified sequence. In preferred embodiments, this term means that the amino acid sequence of the peptide has one amino acid difference (substitution, deletion or insertion) from the specified sequence.

In a preferred embodiment, the peptide of the invention as disclosed above exhibits a skin whitening activity and/or disturbs or inhibits the interaction between AP-1 and KIF13A.

When the peptide of the invention further comprises additional amino acid residues, these residues can be added to the C- and/or N-terminal ends.

The peptide of the invention has from 3 to 15 amino acids in length. Thus, the peptide may have 3, 4, 5, 6, 7, 8, 9, 10, 11, 12, 13, 14 or 15 amino acids in length. Preferably, the peptide has from 3 to 11 amino acids in length, more preferably from 3 to 7 amino acids in length.

In a particular embodiment, the peptide has from 3 to 5 amino acids in length, preferably has 5 amino acids in length.

So as to enhance the stability of the peptide by improving its resistance to peptidases, protective groups may be added to the C- and/or N-terminal ends without altering the activity of the peptide. For example, the protective group at the N-terminal end may be an acylation or an acetylation and the protective group at the C-terminal end may be an amidation or an esterification. The action of proteases may also be blocked by the use of amino acids in the D configuration, cyclisation of the peptide by formation of disulphide bridges, lactam rings or bonds between the C- and N-terminal ends. The peptide of the invention may also comprise pseudo-peptide bonds replacing the "classical" CONH peptide bonds and conferring increased resistance to peptidases, such as $CHOH-CH_2$, NHCO, $CH_2-O$, $CH_2CH_2$, $CO-CH_2$, $N-N$, $CH=CH$, $CH_2NH$, and $CH_2-S$.

The invention also encompasses functional derivatives of a peptide according to the invention such as described above. The term "functional derivative" as employed herein refers to molecules that mimic the chemical structures of a peptide of the invention and retain the functional properties of said peptide. For example, said functional derivatives may be retropeptides, retro-inverso peptides, peptidomimetics such as peptoids or β-peptides, or peptides with methylated amide linkages. Approaches to designing peptide analogs are well known in the art.

The invention also encompasses the physiologically acceptable salts of a peptide according to the invention. Physiologically acceptable salts may, for example, be salts of physiologically acceptable mineral acids such as hydrochloric acid, hydrobromic acid, sulphuric acid and phosphoric acid; salts of physiologically acceptable organic acids such as acetic acid, citric acid, maleic acid, malic acid, succinic acid, ascorbic acid and tartaric acid; salts of physiologically acceptable mineral bases such as salts of sodium, potassium, calcium, magnesium or ammonium; or salts of organic bases which contain a salifiable nitrogen, commonly used in pharmaceutical technique. The methods for preparing said salts are well known to one of skill in the art.

The peptide according to the invention may be obtained by well-known methods such as classical chemical synthesis (in solid phase or homogeneous liquid phase) or by enzymatic synthesis (Kullmann W, 1987, Enzymatic peptide synthesis, CRC Press, Florida). It may also be obtained by the method consisting in culturing a host cell, such as described hereinafter, comprising a transgene coding for the peptide and expressing said peptide, and extracting said peptide from said host cells or from the culture medium into which the peptide was secreted. Peptides of the invention can also be obtained from natural proteins; i.e. by controlled hydrolysis of a protein of animal, vegetable or microbial origin. The hydrolysis may be carried out on a raw extract or on isolated or purified proteins. Thus, the peptide of the invention may be of natural or synthetic origin. Preferably, the peptide is obtained by chemical synthesis.

As used herein, the term "skin whitening", "skin lightening", "skin depigmenting" or "skin bleaching" agent refer to an active agent, i.e. a peptide of the invention, able to inhibit or decrease the synthesis of melanin in melanocytes and thus to whiten the skin. This activity is preferably due to the disturbance or inhibition of the interaction between AP-1 and KIF13A.

The skin whitening activity of the peptide of the invention may be easily determined by assessing the effect of the peptide on the interaction between the AP-1 adaptor complex and KIF13A. In particular, the person skilled in the art may carry out a biochemical assay as disclosed in the experimental section, i.e. a biochemical assay comprising incubating a cell lysate with a peptide of the invention, or a functional derivative or physiologically acceptable salt thereof, immunoprecipitating AP-1 from the cell lysates, and revealing its partner, KIF13A by western blot analysis of this immunoprecipitate. Monoclonal or polyclonal antibodies directed against AP-1, and in particular the γ-adaptin subunit, and KIF13A are commercially available (mouse monoclonal anti-γ-adaptin, Sigma Aldrich; rabbit polyclonal anti-KIF13A, Bethyl Laboratories, Inc.). A peptide of the invention exhibits a skin whitening activity when it is able to disrupt the interaction between the AP-1 adaptor complex and KIF13A, i.e. when co-immunoprecipitation of AP-1 and KIF13A is significantly reduced by comparison with cell lysates incubated without peptide.

Alternatively, the skin whitening activity of the peptide may be determined by immunofluorescence to observe the cellular localization of AP-1 and KIF13A in cells incubated with or without a peptide of the invention. With this assay, a peptide exhibits a skin whitening activity when the cellular colocalization of AP-1 and KIF13A in cells incubated with the peptide is significantly reduced by comparison with cells incubated without peptide.

The skin whitening activity of the peptide may also be determined by electron microscopy to observe the number of mature pigmented melanosomes in cells incubated with or without a peptide of the invention. With this assay, a peptide exhibits a skin whitening activity when the number of mature pigmented melanosomes in cells incubated with the peptide is significantly reduced by comparison with cells incubated without peptide.

The skin whitening activity of the peptide may further be determined by measuring the melanin content of melanocytic cells such as MNT-1 cells, incubated with the peptide. For example, the assay may be carried out as follow: at day 1, $10^5$ MNT-1 cells are seeded in 6-well plates; From day 2 to day 4, cells are grown in medium comprising 10 µM of peptides; at day 5, cells are disrupted by sonication in 50 mM Tris-HCl, pH 7.4, 2 mM EDTA, 150 mM NaCl, 1 mM dithiothreitol, and protease inhibitors. Pigment is pelleted at 20,000 g for 15 min at 4° C., rinsed once in ethanol/ether (1:1), and dissolved in 2 M NaOH/20% dimethylsulfoxide at 60° C.; Melanin content is measured as optical density at 492 nm. With this assay, a peptide of the invention exhibits a skin whitening activity when the amount of melanin in cells incubated with said peptide is significantly reduced by comparison with the melanin content of cells incubated without peptide.

As used herein, the term "significantly reduced" refers to a decrease of at least 10, 15, 20, 25, 30, 35 or 40% of the value obtained with cells incubated without the peptide of the invention, i.e. the value obtained with the control sample wherein the peptide of the invention is replaced with the diluent only, e.g. $H_2O$.

In a preferred embodiment, the peptide of the invention induces a reduction of at least 20%, preferably at least 40%, of the melanin content of melanocytic cells such as MNT-1 cells, incubated with said peptide.

The present invention also relates to a nucleic acid coding for a peptide according to the invention. In the spirit of the invention, "nucleic acid" is understood to mean any molecule based on DNA or RNA. These may be synthetic or semi-synthetic, recombinant molecules, possibly amplified or cloned into vectors, chemically modified, comprising non-natural bases or modified nucleotides comprising for example a modified bond, a modified purine or pyrimidine base, or a modified sugar. The nucleic acid according to the invention may be in the form of DNA and/or RNA, single stranded or double stranded. According to a preferred embodiment, the nucleic acid is an isolated DNA molecule, synthesized by recombinant techniques well known to one of skill in the art. The nucleic acid according to the invention may be deduced from the sequence of the peptide according to the invention and codon usage may be adapted according to the host cell in which the nucleic acid shall be transcribed. These steps may be carried out according to methods well known to one of skill in the art and some of which are described in the reference manual Sambrook et al. (Sambrook J, Russell D (2001) Molecular cloning: a laboratory manual, Third Edition Cold Spring Harbor).

The present invention further relates to an expression cassette comprising a nucleic acid according to the invention operably linked to the sequences required for its expression. In particular, the nucleic acid may be under the control of a promoter allowing its expression in a host cell. Generally, an expression cassette is constituted of or comprises a promoter allowing initiation of transcription, a nucleic acid according to the invention, and a transcription terminator. The term "expression cassette" denotes a nucleic acid construct comprising a coding region and a regulatory region, operably linked. The expression "operably linked" indicates that the elements are combined in such a way that the expression of the coding sequence (the gene of interest) and/or the targeting of the encoded peptide are under the control of the transcriptional promoter and/or signal peptide.

The present invention also relates to an expression vector comprising a nucleic acid or an expression cassette according to the invention. Said expression vector may be used to transform a host cell and enable the expression of the nucleic acid of the invention in said cell. The vector may be a DNA or an RNA, circular or not, single- or double-stranded. Advantageously it is selected from among a plasmid, a phage, a phagemid, a virus, a cosmid and an artificial chromosome. Advantageously, the expression vector comprises regulatory elements allowing the expression of the nucleic acid according to the invention. These elements may contain for example transcriptional promoters, transcriptional activators, terminator sequences, initiation and termination codons. The methods for selecting said elements according to the host cell in which expression is desired, are well known to one of skill in the art. The vector may also contain elements enabling its selection in the host cell such as, for example, an antibiotic resistance gene or a selectable gene providing complementation of the respective gene deleted from the host cell genome. Such elements are well known to one of skill in the art and extensively described in the literature.

The present invention relates to the use of a nucleic acid, an expression cassette or an expression vector according to the invention to transform or transfect a cell. The host cell may be transformed/transfected in a transient or stable manner and the nucleic acid, cassette or vector may be contained in the cell in the form of an episome or in chromosomal form.

The present invention relates to a host cell comprising a nucleic acid, a cassette or an expression vector according to the invention. According to one embodiment, the host cell is a microorganism, preferably a bacterium or a yeast. According to another embodiment, the host cell is an animal cell, for example a mammalian cell such as COS or CHO cells. In a particular embodiment, the cell is non-human and non-embryonic.

The present invention also relates to a method for producing a skin whitening peptide according to the invention comprising transforming or transfecting a cell with a nucleic acid, an expression cassette or an expression vector according to the invention; culturing the transfected/transformed cell; and recovering the peptide produced by said cell. Methods for producing recombinant peptides are well known to one of skill in the art.

The present invention also relates to a method for producing a peptide according to the invention comprising inserting a nucleic acid, a cassette or an expression vector according to the invention in an in vitro expression system also called acellular and recovering the peptide produced by said system. Many in vitro or acellular expression systems are commercially available and the use of said systems is well known to one of skill in the art.

In another aspect, the present invention relates to a cosmetic or pharmaceutical composition comprising a skin whitening peptide of the invention, or a functional derivative or physiologically acceptable salt thereof, and a physiologically acceptable carrier and/or excipient.

Preferably, the formulation of the composition is adapted to topical administration, i.e. the composition is a topical composition.

The term "physiologically acceptable carrier and/or excipient" as used herein, refers to a carrier or excipient that is preferably adapted for topical application onto skin, is compatible with the peptides of the present invention and any other active substances comprised in the composition, and will not cause any untoward safety or toxicity concerns. The carrier or excipient may be cosmetically or pharmaceutically acceptable depending on the desired property profile. The composition of the invention may comprise from about 50% to about 99.99% of carrier(s) and/or excipient(s), preferably from about 80% to about 99.9%, more preferably from about 90% to about 95%.

The composition according to the invention can arise in any galenical form normally used for topical application. In particular, the composition can be solid, semi-solid or liquid.

It may be for instance in the form of a white or colored powder, ointment, paste, cream, fluid, milky lotion, cosmetic water, lotion, serum, aqueous or oily gel, aqueous hydroalcoholic or oily solution, oil in water or water in oil or multiple emulsion, foam, facial mask, watery or anhydrous stick, dispersion of oil in a polymer phase such as nanospheres and nanocapsules.

Optionally, the composition can be applied to the skin in the form of aerosol. It can also be provided as patches, pencils, brushes and applicators for local application on spots of the face or hands. It can be used as a skin-care product and/or a make-up product.

Preferably, the composition includes water. More preferably, the composition is in the form of an oil-in-water, water-in-oil or water-in-silicon emulsion.

When the composition of the invention is an emulsion, the proportion of the oil phase can range from 5% to 80% by weight, and preferably from 5% to 50% by weight compared to the total weight of the composition. The oils, emulsifiers and co-emulsifiers used in the composition in emulsion form are selected among those classically used in the related field. The emulsifier and co-emulsifier are present in the composition in a proportion ranging from 0.3% to 30% by weight, and preferably from 0.5% to 20% by weight compared to the total weight of the composition.

Examples of suitable oils include, but are not limited to, mineral oils such as petrolatum jelly or paraffin oil; oils of vegetable origin such as avocado, soybean or jojoba oil; oils of animal origin such as lanolin; synthetic oils such as alky benzoates and branched hydrocarbons such as polybutene, perhydrosqualene; silicone oils such as cyclomethicones, dimethicones and phenyldimethicones; and fluorinated oils such as perfluoropolyethers. Also of use as fatty matter are fatty alcohols like cetyl alcohol, fatty acids or waxes such as carnauba wax, beeswax, polyethylene wax or ozokerite.

Examples of suitable emulsifiers and co-emulsifiers include, but are not limited to, esters of fatty acid and polyethylene glycol such as PEG-20 stearate and esters of fatty acid and glycerin such as glyceryl stearate.

Alternatively, the peptides of the invention contain in the composition may be encapsulated in liposomes. As used herein, "liposome" means the small vesicles manufactured artificially and made up of phospholipid layers, separated from each other by aqueous compartments. They have a structure very close to that of cell membranes, which enables them to merge with them while releasing the active ingredients that they contain. Examples of suitable liposomes include, but are not limited to, multilamellar liposomes or MLV (MultiLamellar Vesicles), small unilamellar liposomes or SUV (Small Unilamellar Vesicles), or large unilamellar liposomes or LUV (Large Unilamellar Vesicles), or SECosomes (surfactant-ethanol-cholesterol-osomes) as described in Geusens et al., 2010 (Advanced Functional Materials. 2010. pp. 4077-4090). The liposomes can also be nonionic liposomes whose wall does not consist of phospholipids but rather nonionic lipids.

The composition may also comprise other additives including, but being not limited to, silicone elastomers, surfactants, thickeners, gelling agents, humectants, agents facilitating percutaneous absorption, colorants, preservatives, optical modifiers, chelating agents such as the salts of EDTA and/or fragrances. Examples of such additives and others are cited in the International Cosmetic Ingredient Dictionary & Handbook, 15th Edition, 2014, published by the Personal Care Products Council. The quantities of these various additives are those classically used in the related fields. These additives, according to their nature, can be introduced into the oil phase, the aqueous phase, lipid vesicles and/or nanoparticles.

Alternatively, the composition of the invention may also be adapted to parenteral administration, i.e. the composition may be an injectable composition. The term "injectable composition," as used herein, means a composition suitable for injection into humans and/or animals, wherein the injection is preferably intradermal or subcutaneous. These compositions have to be sterile, pyrogen free, and at a physiologically acceptable pH. Suitable injectable formulations may contain preservatives, such as sodium benzoate, methylparaben and propylparaben, etc., and may have a pH of 6.8-8.0 at 25 Degrees C. The pH is preferably maintained by a buffer. Suitable buffering agents include acetate buffers, 2-amino-2-methyl-1-propanol, glycine buffers, phosphate buffers, TRIS buffers, etc.

The composition may comprise one or several, e.g. 2, 3, 4 or 5, peptides of the invention, or functional derivatives or physiologically acceptable salts thereof. In a preferred embodiment, the composition comprises at least a peptide comprising, or consisting of, the amino acid sequence QVAVK (SEQ ID NO: 16).

The composition comprises an effective amount of peptides of the invention. The term "effective amount" as used in the present application is a quantity of skin whitening peptide of the invention enabling a significant decrease in the synthesis of melanin. This decrease can, in particular, result in a visible change in the color of the skin. This decrease can, for example, be 5%, 10%, 15%, 20%, 25%, 30%, 35% or 40% of the quantity of melanin present in untreated cells. For instance, the effective amount may be from 0.001 to 20% by weight, preferably from 0.01% to 10% by weight, and more preferably from 0.1 to 5% by weight, relative to the total weight of the composition.

The composition of the invention may further comprise one or several additional active substances.

In an embodiment, the peptides of the present invention are mixed with one or several other skin whitening agents. Examples of such whitening agents include, but are not limited to, ellagic acid (Kamide et al. Nishinihon J Dermatol. 1995; 57:136-142), arbutin (Sugai et al. Skin Res (Hifu) 1992; 34:522-529), resorcinol, rucinol (4-n-butylresorcinol) (Katagiri et al. J Cosmet Chem Jpn. 2001; 35:42-49), kojic acid (Mishima et al. Skin Res (Hifu) 1994; 36:134-150), placental extracts (Itoh. Fragrance J. 1990:6, 67-71), plant extracts including *Narcissus tazetta, Morus alba, Phyllanthus emblica, Catharanthus roseus, Fomes japonicus, Ganoderma, Chamomilla* (Kawashima et al. Nishinihon J Dermatol. 1999; 61:682-685) and *Glycyrrhiza glabra* (licorice) extracts, glabridin, ascorbic acid and its derivatives such as L-ascorbic acid-2-phosphate, sodium L-ascorbic acid-2-phosphate, L-ascorbic acid 2-glucoside, and L-ascorbic acid ethyl ester (Maeda et al. J Jpn Cosmet Sci Soc. 2003; 27:257-268; Kumano et al. J. Nutr. Sci. Vitaminol. 1998; 44:345-359; Kameyama et al. J. Am. Acad. Dermatol. 1996; 34:29-33; Miyai et al. Nishinihon J Dermatol. 1996; 58:439-443), linoleic acid (Shigeta et al. Biol. Pharm. Bull. 2004; 27:591-594), tranexamic acid (Mafune et al. Farumashia. 2008; 44:437-442), tranexamic acid cetyl ester hydrochloride, 4-methoxy potassium salicylate, adenosine monophosphate disodium salt (Kawashima et al. Jpn J Clin Dermatol. 2008; 62:250-257), 5,5'-dipropyl-biphenyl-2,2'-diol (Magnolias®) (Takeda et al. Nishinihon J Dermatol. 2006; 68:293-298), 4-(4-hydroxyphenyl)-2-butanol, cysteine, 4-thioresorcin (EP 0623341), 5-hydroxy-2-hydroxymethyl-γ-pyridone, niacinamide, iminophenols (WO 99/22707), carnitine and/or quinone (DE 19806947), amino-phenol amide derivatives (FR 2772607), benzothiazole derivatives (WO 99/24035), pantothenate, glycyrrhizinic acid, hydroquinone-beta-glucoside and inulavosin (Pigment Cell Melanoma Res. 2014 May; 27(3):376-86).

The composition may also comprise additional active substances aimed at reinforcing the desired effects such as, for example, organic or inorganic sunscreens; keratolytic and/or exfoliating agents such as salicylic, glycolic, lactic, citric, malic acid; moisturizers; emollients; astringents; antiseptics; anti-glycation and/or antioxidant agents such as tocopherol, thiotaurine, hypotaurine, aminoguanidine, thiamin pyrophosphate, pyridoxamine, lysine, histidine, arginine, phenylalanine, pyridoxine, adenosine triphosphate; polyols such as glycerin, glycol or propylene glycol; vitamins such as vitamin A, E, K; retinoic acid, retinaldehyde, retinol; palmitate, propionate or acetate; hyaluronic acid; anti-inflammatory agents; soothing agents; and/or deoxyribonucleic or ribonucleic acids.

The present invention also relates to the use of a peptide according to the invention, a functional derivative or a physiologically acceptable salt thereof, as cosmetic agent, in particular as skin whitening cosmetic agent.

The invention further relates to a cosmetic method for whitening human skin, comprising topically applying onto human skin a cosmetic composition of the invention.

Preferably, the cosmetic composition of the invention is applied every day, more preferably twice a day.

The invention also relates to a cosmetic method for whitening human skin, comprising parenteral administration of a cosmetic composition of the invention. Preferably, the composition is intradermally or subcutaneously administered.

In another aspect, the present invention relates to a skin whitening peptide of the invention as medicament.

The present invention also relates to a peptide or composition of the invention for use in the prevention or treatment of hyperpigmentation.

It further relates to a method for treating hyperpigmentation comprising administering an effective dose of a peptide or composition of the invention to a subject in need thereof. The invention also relates to a use of a peptide or composition of the invention for manufacturing a medicament for the treatment or the prevention of hyperpigmentation.

Preferably, the subject to be treated is a mammal, more preferably a human.

Hyperpigmentation is characterized by an accumulation of melanin and often results in irregular pigmentation pattern. In particular, the peptide or composition of the invention may be used to whiten skin of pigmented spots and thus uniformize the skin pigmentation of the subject. Hyperpigmentation may be selected from the group consisting of melasma such as idiopathic melasma (i.e. melasma not associated with pregnancy or with taking oral contraceptives) or chloasma (also named mask of pregnancy), actinic lentigo (also called senile lentigo, senile spots, sun spots, age spots or lentigo), pigmentary after-effects from acne, post-inflammatory pigmentations due to an abrasion, a burn, a scar, pigmentations due photosensitization, dermatosis and/or contact allergy, meadows dermatitis, pigmentations due to poison ivy, freckles, and nevi such as congenital giant nevus, Becker nevus or Spitz nevus.

Further aspects and advantages of the present invention will be described in the following examples, which should be regarded as illustrative and not limiting.

EXAMPLES

Materials and Methods

Peptides Design and Preparation

The inventors designed peptides of 11, 5 or 3 amino acids spanning the region located between the 813$^{rd}$ and 890$^{th}$ amino acids of the β1-adaptin subunit of human AP-1.

All the peptides were synthesized by Proteogenix (Oberhausbergen, France). Lyophilized peptides were diluted either in H$_2$O or in dimethylsulfoxide (DMSO)/H$_2$O (1 v/3 v) according to manufacturer's recommendations. The table below presents the peptides sequences.

| Peptides name | Peptides sequence |
|---|---|
| AI-11 | APLSPNQTVEI (SEQ ID NO: 17) |
| QT-11 | QTVEISLPLST (SEQ ID NO: 18) |
| LK-11 | LPLSTVGSVMK (SEQ ID NO: 19) |
| GN-11 | GSVMKMEPLNN (SEQ ID NO: 20) |
| EK-11 | EPLNNLQVAVK (SEQ ID NO: 1) |
| QF-11 | QVAVKNNIDVF (SEQ ID NO: 21) |
| NY-11 | NIDVFYFSTLY (SEQ ID NO: 22) |
| FF-11 | FSTLYPLHILF (SEQ ID NO: 23) |
| LM-11 | LHILFVEDGKM (SEQ ID NO: 24) |
| EL-11 | EDGKMDRQMFL (SEQ ID NO: 25) |
| RI-11 | RQMFLATWKDI (SEQ ID NO: 26) |
| WQ-11 | WKDIPNENEAQ (SEQ ID NO: 27) |
| EN-5 | EPLNN (SEQ ID NO: 10) |
| NV-5 | NNLQV (SEQ ID NO: 13) |
| SS-5 | STVGS (SEQ ID NO: 28) |
| QK-5 | QVAVK (SEQ ID NO: 16) |
| EL-3 | EPL |
| LN-3 | LNN |
| QA-3 | QVA |
| AK-3 | AVK |

Cell Culture

HeLa cells were maintained in DMEM supplemented with 10% FBS and antibiotics (Invitrogen). MNT-1 cells were maintained in DMEM supplemented with 10% AIM-V medium, 20% FCS, nonessential amino acids, sodium pyruvate and antibiotics (Invitrogen).

Protein Extractions, Immunoprecipitation and Western-Blot Analyses.

Cells at 80% of confluency were washed in cold PBS and lysed on ice in lysis buffer (50 mM Tris, 150 mM NaCl, 0.1% Triton X-100, 10 mM EDTA, pH 7.2, and protease inhibitor cocktail, Roche). Lysates were incubated overnight with 1 µg of peptides. Lysates were first precleared using protein G agarose beads for 1 h at 4° C. under rotation. Supernatants were collected and incubated with protein G agarose beads with 1 µg mouse monoclonal IgG2b anti-CD9 for 1 h at 4° C. under rotation. Precleared supernatants were incubated with beads coated earlier with 1 µg mouse monoclonal IgG2b anti-γ-adaptin for 2 h at 4° C. under rotation. As negative control, 1 µg mouse monoclonal IgG2b anti-CD9 was used to immunoprecipitate the lysate.

After five washes in cold lysis buffer and three washes in PBS, immunoprecipitated proteins bound to the beads were incubated in sample buffer with reducing agent, boiled for 10 min at 95° C., and fractionated by SDS-PAGE using Nupage (3-8%) Tris-acetate gels (Invitrogen). Transfer was realized on nitrocellulose membrane (Millipore). Membranes were probed with mouse monoclonal anti-γ-adaptin (Sigma-Aldrich) and rabbit polyclonal to KIF13A (Bethyl Laboratory, Inc.).

Immunofluorescence

MNT-1 cells grown on coverslips were incubated for three days in medium containing 10 µg of peptides. Coverslips were rinsed in PBS, fixed in 100% cold methanol for 30 sec, followed by incubation in PBS and 1 mg/ml BSA. Fixed cells were washed in PBS, quenched for 10 min in PBS and 50 mM glycine at RT, saturated in blocking buffer, and permeabilized in PBS, 0.05% saponin, and 1 mg/ml BSA (incubation buffer, IB). Cells were incubated for 1 h with mouse monoclonal anti-γ-adaptin (Sigma-Aldrich) and rabbit polyclonal to KIF13A (Bethyl Laboratory, Inc.) diluted in IB, washed three times in IB, and incubated with the corresponding secondary antibodies (Alexa Fluor, Invitrogen) for 30 min. Cells were washed twice in IB and once in blocking buffer. Finally, coverslips were mounted in DABCO medium and examined under a 3D Nikon microscope.

Colocalization analysis was performed using ImageJ software. First, a merged image was generated using Colocalization Plugin. Only pixels were intensity of the overlay exceed the intensity of individual channel were considered as colocalizing pixels. Then identical area inside cells were defined and analyzed for quantification.

Conventional Electronic Microscopy

Control and peptide-treated MNT-1 cells grown on coverslips for 3 days were fixed with 2.5% glutaraldehyde in 0.1M cacodylate buffer, pH 7.2 post-fixed with 1% OsO$_4$ supplemented with 1.5% Potassium ferrocyanure, dehydrated in ethanol, and embedded in epon. Ultrathin sections were prepared with an Ulltracut UCT ultramicrotome (Leica) and observed under a CM120 electron microscope (FEI company, Eindoven) after counter-staining with uranyl acetate and lead citrate.

Grading of melanosomes stages from I to IV, based on morphology and melanin content, were done independently by two authors. The table below presents the criteria of analyses.

| Stage | Criteria |
|---|---|
| I | Spherical, no melanin |
| II | Oval, parallel filament |
| III | Oval, moderate deposit of melanin |
| IV | Oval, intense deposit of melanin |

Melanin Assay

On MNT-1 Cells

At day 1, 10$^5$ cells were seeded in 6-well plates. From day 2 to day 4, cells were grown in medium containing 1 or 10 µg of peptides. Medium was changed every day. At day 5, cells were disrupted by sonication in 50 mM Tris-HCl, pH 7.4, 2 mM EDTA, 150 mM NaCl, 1 mM dithiothreitol, and protease inhibitors. Pigment was pelleted at 20,000 g for 15 min at 4° C., rinsed once in ethanol/ether (1:1), and dissolved in 2 M NaOH/20% dimethylsulfoxide at 60° C. Melanin content was measured as optical density at 492 nm.

On Reconstructed Epidermis

Reconstructed human epidermal of phototype VI (Sterlab) were received at day 10 and incubated with the manufacturer's growth medium supplemented from day 11 to day 21 with 30 μg of peptides. As recommended, medium was changed every day. At day 21, the epidermis was separated from the insert, digested by incubation in 400 μl of Solvable (PerkinElmer) at 98° C. for 1 h. Melanin content was measured as optical density at 492 nm.

Results

The inventors designed small peptides aiming at blocking the interaction of the AP-1 complex with the kinesin KIF13A. This interaction has been shown to be critical for the transport of melanogenic enzymes to the melanosomes and then to be required for the pigmentation of human skin melanocytes (Delevoye et al., J Cell Biol. 2009 Oct. 19; 187(2):247-64). The inventors herein show that peptides as small as 5 or 3 amino acids (aa) are able to prevent the interaction between AP-1 complex and KIF13A as well as their intracellular co-localization, resulting in a decrease of the number of pigment granules by skin melanocytes and a reduction of the intracellular melanin content of skin melanocytes as well as in synthetic human pigmented skin epidermis.

EK-11 Peptides Decrease the Interaction of KIF13A with AP-1 Complex

Figure 1:
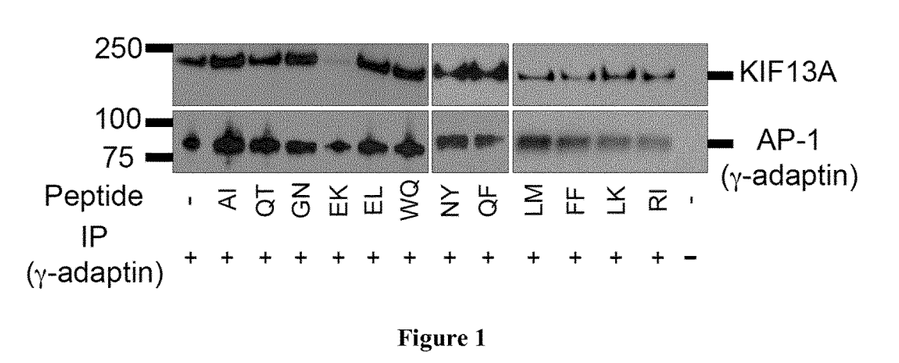
FIG. 1: γ-adaptin subunit of the human AP-1 complex was immunoprecipitated from HeLa cell lysates in presence or not of 1 μg of the indicated 11 amino acids peptides (peptides AI, QT, GN, EK, EL, WQ; NY, QF, LM, FF, LK and RI: SEQ ID NO: 17, 28, 20, 1, 25, 27, 22, 21, 24, 23, 19 and 26, respectively) for 2 h at 4° C. under rotation. Immunoprecipitates were loaded on gels for western blot analysis by revealing its partner, using a specific anti-Human KIF13A. Molecular weight in kDa.
Figure 2:
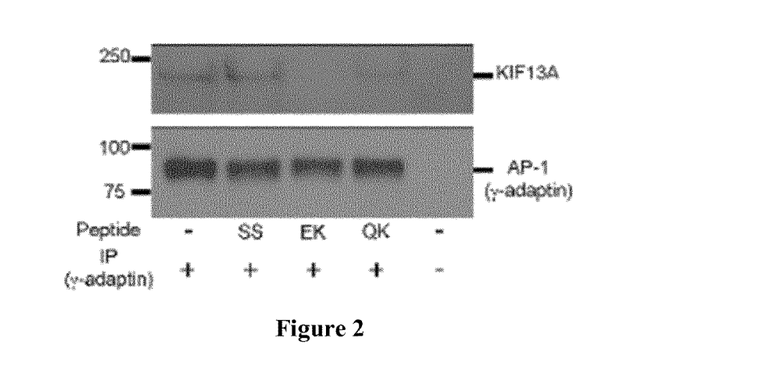
FIG. 2: γ-adaptin subunit of the human AP-1 complex was immunoprecipitated from melanocytes (MNT1) cell lysates in presence or not of 1 μg of the indicated peptides (peptides SS-5, EK-11 and QK-5: SEQ ID NO: 28, 1 and 16, respectively) for 2 h at 4° C. under rotation. Immunoprecipitates were loaded on gels for western blot analysis by revealing its partner, using a specific anti-Human KIF13A. EK-11 and SS-5 peptides were used as a positive and negative controls, respectively. Molecular weight in kDa.

Based on previous work from (Nakagawa et al., Cell, 2000, vol. 103, 569-581), the binding domain of the β1-adaptin subunit of the mouse AP-1 complex with mouse KIF13A was predicted to correspond to a 77 as region located between the $783^{rd}$ and $860^{th}$ aa. The inventors identified the homologous sequence of the human β1-adaptin subunit that corresponds to a 77 aa region ($813^{rd}$-$890^{th}$). Using this 77 aa human sequence, the inventors designed 12 peptides of 11 amino acids sharing 5 amino acids with the adjacent peptides. The inventors tested these sequences for their ability to block the interaction of human AP-1 with human KIF13A. These proteins are ubiquitously expressed, thus the inventors performed a first interaction screen by incubating independently g of each 12 peptides with HeLa cell lysates (non pigmented cells). The γ-subunit of the AP-1 complex was immunoprecipitated from the lysates and immunoprecipitates were tested for their KIF13A content. The inventors showed that only the incubation of the EK-11 peptide (SEQ ID NO: 1) with HeLa cells lysates is able to decrease significantly the interaction of AP-1 with KIF13A about 52.6±7% as compared to control or other designed peptides (FIG. 1). Moreover, the inventors also confirm that the EK-11 peptide decreases the AP-1/KIF13A interaction in skin melanocytic MNT-1 cell lysates (57.5±8%), as much as in HeLa cells (FIG. 2).

QK-5 Peptides Decrease the Interaction of KIF13A with AP-1 Complex

Figure 3:
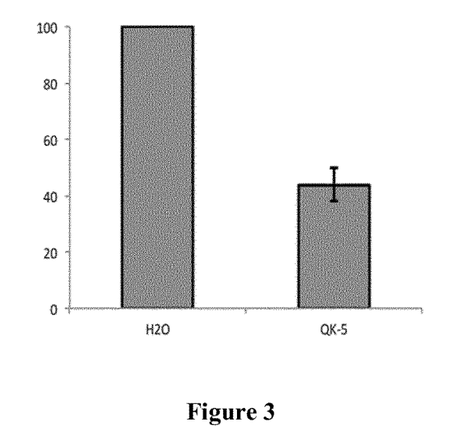
FIG. 3: Intensity of the immunoprecipitated KIF13A and AP-1 bands shown in FIG. 2 were quantified using ImageJ. KIF13A intensity were divided by its corresponding AP-1 intensity and normalized to the control (lysates incubated without peptides, first lane).

In order to find molecules that could be used for industrial purpose, the inventors designed penta-peptides covering and surrounding the EK-11 peptide in order to find shorter peptides able to prevent the AP-1/KIF13A interaction. The inventors showed that the QK-5 peptides (SEQ ID NO: 16) that correspond to the last 5 amino acids of the EK-11 peptide (SEQ ID NO: 1) decrease the ability of AP-1 to interact with KIF13A (FIG. 2) in melanocytic cell lysates (56.1±6%; FIG. 3) as compared to control or other 5aa peptides such as the SS-5 peptide (SEQ ID NO: 28) (FIG. 2). Interestingly, the fold reduction is equivalent to the one generated by the EK-11 peptide incubation (see above). Altogether, the inventors show that the QK-5 peptides prevent the interaction of AP-1 with KIF13A in melanocytes.

QK-5 Peptides Decrease the Colocalization of AP-1 with KIF13A in Skin Melanocytes.

Figure 5:
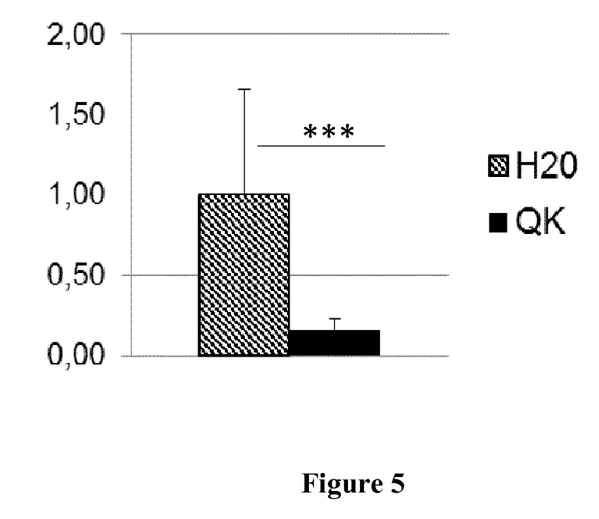

The inventors tested whether the decrease of the interaction of AP-1 with KIF13A (FIG. 3) might be reflected by a decrease of their colocalization in skin melanocytes. QK-5 peptides were incubated with skin melanocytes as described above and immuno fluorescence experiments were performed in order to quantify the colocalization of AP-1 with KIF13A in skin MNT-1 melanocytes. The inventors show that the incubation of the QK-5 peptides decreases the colocalization between both proteins about 84±7% (FIG. 5; p<0.001) as compared to control showing that physical disruption of their interaction (FIG. 2) is followed by a spatial segregation of their intracellular distribution.

QK-5 Peptides Decrease the Melanin Production by Skin Melanocytes

Figure 4:
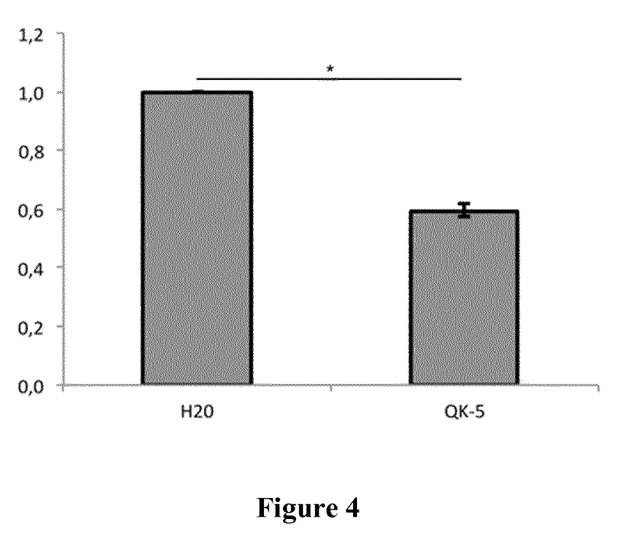
FIG. 4: MNT1 melanocytes were cultured 3 days with 10 μM of QK-5 peptide (SEQ ID NO: 16) or $H_2O$ as a control. Melanin estimation was performed as previously described (Delevoye et al., J Cell Biol. 2009 Oct. 19; 187(2):247-64), and normalized to the control. QK-5 peptide incubation decreased the intracellular melanin content about 40±0.02%. Data are presented as mean±standard deviation. *; p value (two tailed)<0.05.

The inventors previously showed that the AP-1/KIF13A couple is required for the intracellular production of melanin pigment by skin melanocytes (Delevoye et al., J Cell Biol. 2009 Oct. 19; 187(2):247-64). Thus, the inventors tested whether the incubation of the QK-5 peptides can affect the intracellular melanin content of skin MNT-1 melanocytes. MNT1 melanocytes were cultured for 3 days in medium containing 10 μM of the QK-5 peptide (incubation renewed daily), then the intracellular melanin was purified and measured by reading its optical density at 492 nm. The incubation of the QK-5 peptides decreases the intracellular melanin content of skin MNT-1 melanocytes about 40% as compared to control (FIG. 4; p<0.05). This result suggests that the QK-5 peptides diffuse freely into the cells, and show that by blocking the interaction of KIF13A with AP-1, QK-5 decreases consequently the melanin production by treated-melanocytes.

QK-5 Peptides Decrease the Formation of Fully Mature Pigment Granules

Figure 6:
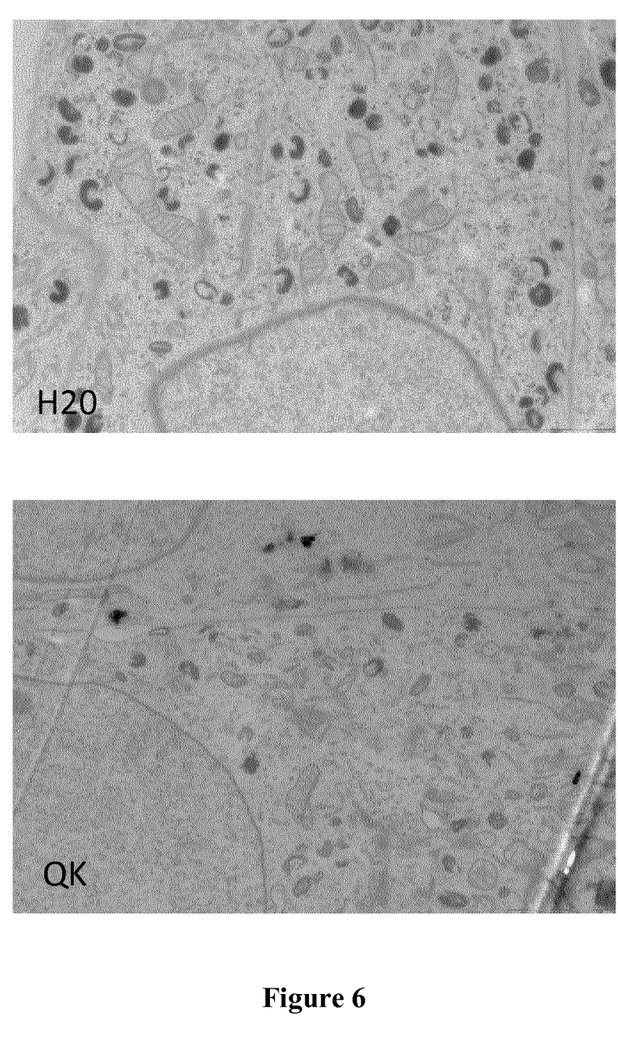
FIG. 6: MNT1 melanocytes were seeded on glass coverslips and cultured 3 days with 10 μM of QK-5 peptide (SEQ ID NO: 16; bottom panel) or $H_2O$ (top panel) as a control. Then cells were rapidly washed in DMEM at room temperature and fixed for 90 min with a mixture of 2.5% glutaraldehyde in 0.1 M cacodylate buffer for 90 min at 4° C., post-fixed with 1% $OsO_4$/1.5% potassium ferrocyanide 45 min at 4° C., dehydrated in ethanol and embedded in Epon resin. Ultrathin (60-70 nm) sections were observed under a CM120 electron microscope (FEI company, Eindoven), equipped with a KeenView camera (Soft Imaging System; SIS, Germany). Melanocytes incubated with QK-5 peptide (bottom panel) harbored fewer dark-pigmented granules (melanosomes) as compared to control (top panel). Scale bar: 2 μm.
Figure 7:
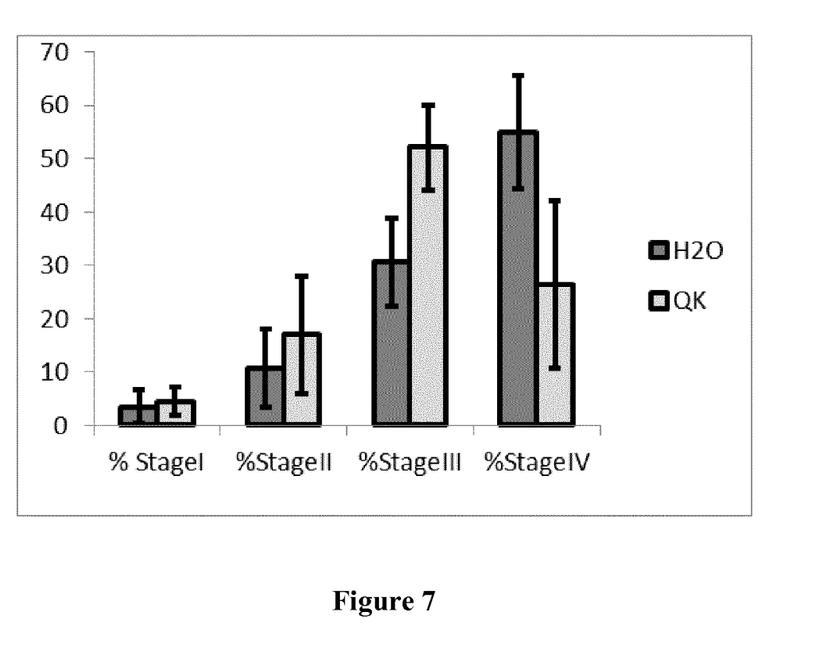
FIG. 7: Melanosome stages were quantified based on their morphologies on MNT1 melanocytes treated as in FIG. 6. Stages I and II correspond to early non-pigmented melanosomes, melanin pigmentation is initiated in stage III, whereas stage IV is a fully mature and pigmented melanosome. Stages were counted and plotted as percentage of their total number. Melanocytes incubated with QK-5 peptide decreased the number of stage IV melanosomes and concomitantly increased the number of less mature and pigmented stages III as compared to control.

In skin melanocytes, melanin synthesis occurred in membrane-bound organelles, called melanosomes (Raposo and Marks, Nat Rev Mol Cell Biol. October 2007; 8(10): 786-797). The inventors previously showed that the AP-1/KIF13A couple is required for the formation of fully pigmented melanosomes (Delevoye et al., J Cell Biol. 2009 Oct. 19; 187(2):247-64). Then the inventors tested whether the incubation of the QK-5 peptides that abolish the interaction and the colocalization of AP-1 with KIF13A (FIGS. 2, 3 and 5) might affect the maturation of melanosomes and in consequence decrease the pigmentation (FIG. 4). QK-5 peptides were incubated with skin melanocytes as described above and processed for electron microscopy (see material and methods). Based on their morphologies, melanosomes exist in 4 different stages, from early non-pigmented melanosomes (Stages I and II) to early mature melanosomes (Stage III, in which melanin start to be deposited into their lumen) then to fully mature melanosomes (Stage IV, in which melanin fills entirely the lumen of the melanosome). MNT-1 cells incubated with the QK-5 peptides for 3 days (FIG. 6, bottom panel) harboured fewer dark pigmented granules (Stage IV melanosomes) as compared to control (FIG. 6, top panel) showing that the maturation of fully pigmented melanosomes is affected in QK-5-treated cells. The inventors quantified the number of melanosomes stages (presented as a % of the total number) in $H_2O$— or QK-5-treated MNT1 cells. As compared to control, QK-5-treated melanocytes increased their number of Stage III and decreased their number of Stage IV melanosomes without affecting the early Stages (I and II) (FIG. 7). This data suggests that the maturation rate of fully pigmented Stage IV melanosomes is slowing down when cells are treated with the QK-5 peptides and explain the decrease of pigmentation shown in FIG. 4.

Three Amino Acids QK-Derived Peptides Decrease Pigmentation of Skin Melanocytes

Figure 8:
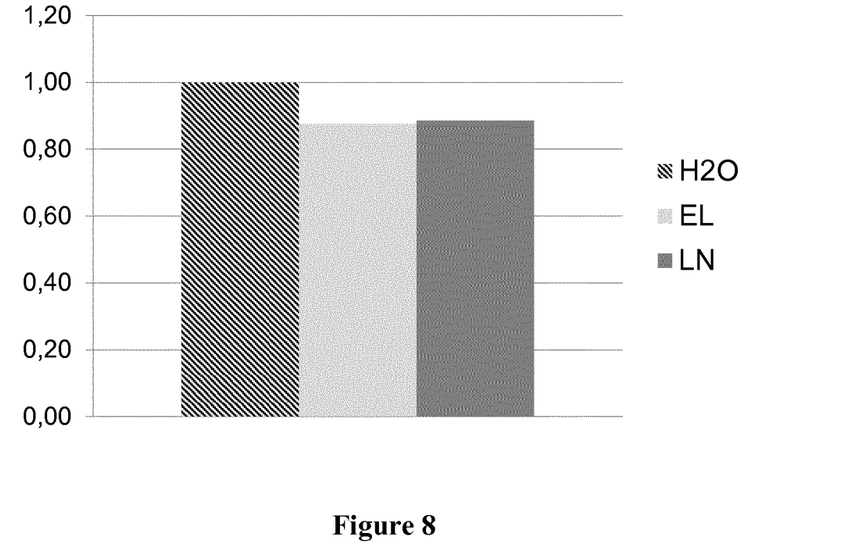
FIG. 8: MNT1 melanocytes were cultured 3 days with 10 µM of either EL-3 or LN-3 or H₂O as a control. Melanin estimation was performed as previously described (Delevoye et al., J Cell Biol. 2009 Oct. 19; 187(2):247-64), and normalized to the control. EL-3 or LN-3 peptide incubation decreased the intracellular melanin content about 12% as compared to control.
Figure 9:
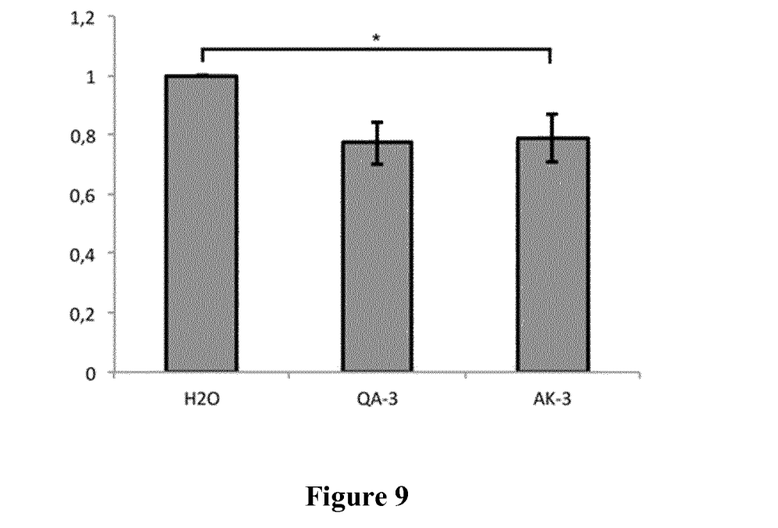
FIG. 9: MNT1 melanocytes were cultured 3 days with 10 µM of QA-3 peptides or AK-3 peptides or H₂O as a control. Melanin estimation was performed as previously described (Delevoye et al., J Cell Biol. 2009 Oct. 19; 187(2):247-64), and normalized to the control. QA-3 and AK-3 peptide incubations decreased the intracellular melanin content about 22.8±7% and 21.3±8% respectively. Data are presented as mean±standard deviation. *; p value (two tailed) <0.05.
Figure 10:
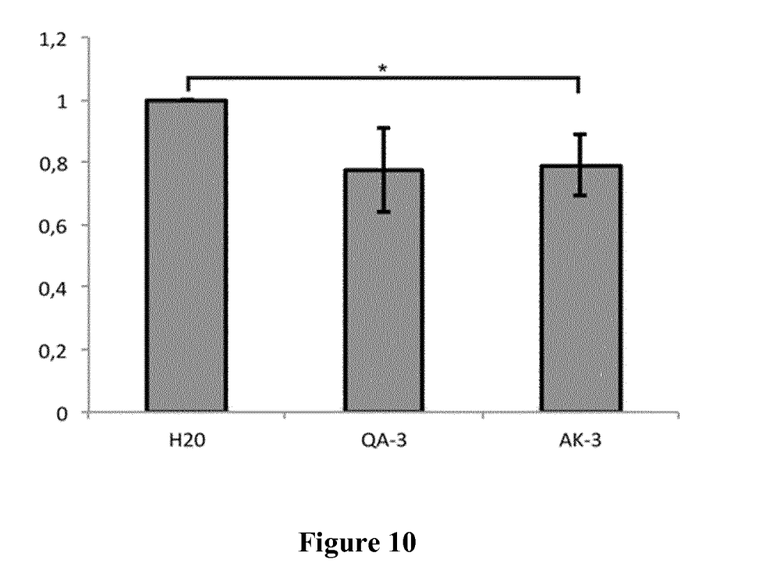
FIG. 10: Melanin quantitation on 3D human reconstructed pigmented epidermis incubated 10 days with 30 µM of QA-3 peptides or AK-3 peptides. Synthetic epidermis were removed from their insert and dissolved in 400 µl of Solvable (Perkin Elmer) for 1 h at 100° C. Melanin quantification was performed on 200 µl by measuring the optical density at 492 nm. Melanin quantifications were normalized to the control. Both QA-3 and AK-3 peptides decreased about 22.5±13% or 21±10% the melanin production by synthetic skin epidermis. Data are presented as mean±standard deviation. *; p value (two tailed)<0.1.

In order to find smaller active molecule, the inventors designed several tri-peptides that derived from the EK-11 peptides and consequently from the two penta-peptides EN-5 and QK-5, namely EL-3 (EPL), LN-3 (LNN), QA-3 (QVA) and AK-3 (AVK) peptides, in order to test their ability to decrease pigmentation. The inventors showed that the incubation of EL-3 or LN-3 decrease moderately the melanin production by skin melanocytes ($\approx$12%) (FIG. 8). Furthermore, the inventors incubated the tri-peptides derived from the QK-5 peptide (QA-3 and AK-3) with skin MNT-1 melanocytes. The inventors show that both QA-3 and AK-3 peptides decreases the intracellular melanin content about 20% (FIGS. 9; 23±7% and 22±8%, respectively; *, $p<0.05$). Moreover, the inventors kept in culture human reconstructed pigmented epidermis in presence of 30 μM of individual tri-peptides. The inventors showed that both QA-3 and AK-3 peptides decrease about 20% the pigmentation of 3D-human reconstructed pigmented epidermis as compared to control (FIGS. 10; 22.5±13% and 21±10% respectively; *, $p<0.1$). This results show that peptides derived from the QK-5 and as small as three amino acids are able to decrease the pigmentation of skin melanocytes as well as synthetic epidermis.

CONCLUSION

The inventors herein demonstrated that peptides as small as 5 or 3 amino acids (aa) derived from the EK-11 peptide, are able to block the interaction of the AP-1 complex with the kinesin KIF13A. These peptides affect not only the physical association of these proteins but also their spatial intracellular co-localization. Because AP-1 and KIF13A are critical for sustaining the maturation of melanosomes and the pigmentation of skin melanocytes, the inventors showed that such peptides affect the pigmentation of skin melanocytes by controlling the maturation rate of fully pigmented melanosomes. The inventors also showed that these peptides decrease the pigmentation of skin melanocytes and importantly, of human reconstructed pigmented epidermis. Altogether, the inventors showed that small peptides inhibiting the interaction of AP-1 with KIF13A are relevant new tools to modulate the human skin pigmentation and can be used as new whitening active molecules.

The invention claimed is:

1. A method of whitening skin comprising topically applying a peptide selected from the group consisting of a peptide up to 15 amino acids in length that contains the sequence of SEQ ID NO: 1, and a peptide up to 5 amino acids in length that contains the sequence AVK, VAVK (SEQ ID NO: 9), QVA or QVAVK (SEQ ID NO: 16), or a physiologically acceptable salt thereof to the skin of a human, as skin whitening cosmetic agent.

2. The method of claim 1, wherein the peptide is up to 5 amino acids in length and contains the amino acid sequence AVK.

3. The method of claim 2, wherein the peptide is up to 5 amino acids in length and contains an amino acid sequence selected from the group consisting of the amino acid sequences AVK, VAVK (SEQ ID NO: 9) and QVAVK (SEQ ID NO: 16).

4. The method of claim 2, wherein the peptide consists of an amino acid sequence selected from the group consisting of the amino acid sequences AVK, VAVK (SEQ ID NO: 9) and QVAVK (SEQ ID NO: 16).

5. The method of claim 1, wherein the peptide is of up to 5 amino acids in length and contains the amino acid sequence QVA or QVAVK (SEQ ID NO: 16).

6. A method of treating hyperpigmentation comprising topically applying a peptide selected from the group consisting of a peptide up to 15 amino acids in length that contains the sequence of SEQ ID NO: 1, and a peptide of up to 5 amino acids in length that contains the sequence AVK, VAVK (SEQ ID NO: 9), QVA or QYAVK (SEQ ID NO: 16), or a physiologically acceptable salt thereof to the skin of a human having hyperpigmentation.

7. The method of claim 6, wherein the hyperpigmentation is selected from the group consisting of melasma, actinic lentigo, pigmentary after-effects from acne, pigmentations due photosensitization, post-inflammatory pigmentations due to an abrasion, a burn, a scar, dermatosis and/or contact allergy, meadows dermatitis, pigmentations due to poison ivy, freckles, nevi, congenital giant nevus, Becker nevus or Spitz nevus.

8. The method of claim 1, wherein the peptide consists of the amino acid sequence QVA or QVAVK (SEQ ID NO: 16).

9. The method of claim 1, wherein the peptide consists of the amino acid sequence QVA.

10. The method of claim 1, wherein the peptide consists of the amino acid sequence QVAVK (SEQ ID NO: 16).

* * * * *

SEQUENCE LISTING

```
<160> NUMBER OF SEQ ID NOS: 28

<210> SEQ ID NO 1
<211> LENGTH: 11
<212> TYPE: PRT
<213> ORGANISM: Homo sapiens

<400> SEQUENCE: 1

Glu Pro Leu Asn Asn Leu Gln Val Ala Val Lys
1               5                   10

<210> SEQ ID NO 2
<211> LENGTH: 4
<212> TYPE: PRT
<213> ORGANISM: Homo sapiens

<400> SEQUENCE: 2

Glu Pro Leu Asn
1

<210> SEQ ID NO 3
<211> LENGTH: 4
<212> TYPE: PRT
<213> ORGANISM: Homo sapiens

<400> SEQUENCE: 3

Pro Leu Asn Asn
1

<210> SEQ ID NO 4
<211> LENGTH: 4
<212> TYPE: PRT
<213> ORGANISM: Homo sapiens

<400> SEQUENCE: 4

Leu Asn Asn Leu
1
```

```
<210> SEQ ID NO 5
<211> LENGTH: 4
<212> TYPE: PRT
<213> ORGANISM: Homo sapiens

<400> SEQUENCE: 5

Asn Asn Leu Gln
1

<210> SEQ ID NO 6
<211> LENGTH: 4
<212> TYPE: PRT
<213> ORGANISM: Homo sapiens

<400> SEQUENCE: 6

Asn Leu Gln Val
1

<210> SEQ ID NO 7
<211> LENGTH: 4
<212> TYPE: PRT
<213> ORGANISM: Homo sapiens

<400> SEQUENCE: 7

Leu Gln Val Ala
1

<210> SEQ ID NO 8
<211> LENGTH: 4
<212> TYPE: PRT
<213> ORGANISM: Homo sapiens

<400> SEQUENCE: 8

Gln Val Ala Val
1

<210> SEQ ID NO 9
<211> LENGTH: 4
<212> TYPE: PRT
<213> ORGANISM: Homo sapiens

<400> SEQUENCE: 9

Val Ala Val Lys
1

<210> SEQ ID NO 10
<211> LENGTH: 5
<212> TYPE: PRT
<213> ORGANISM: Homo sapiens

<400> SEQUENCE: 10

Glu Pro Leu Asn Asn
1               5

<210> SEQ ID NO 11
<211> LENGTH: 5
<212> TYPE: PRT
<213> ORGANISM: Homo sapiens

<400> SEQUENCE: 11

Pro Leu Asn Asn Leu
1               5

<210> SEQ ID NO 12
<211> LENGTH: 5
```

```
<212> TYPE: PRT
<213> ORGANISM: Homo sapiens

<400> SEQUENCE: 12

Leu Asn Asn Leu Gln
1               5

<210> SEQ ID NO 13
<211> LENGTH: 5
<212> TYPE: PRT
<213> ORGANISM: Homo sapiens

<400> SEQUENCE: 13

Asn Asn Leu Gln Val
1               5

<210> SEQ ID NO 14
<211> LENGTH: 5
<212> TYPE: PRT
<213> ORGANISM: Homo sapiens

<400> SEQUENCE: 14

Asn Leu Gln Val Ala
1               5

<210> SEQ ID NO 15
<211> LENGTH: 5
<212> TYPE: PRT
<213> ORGANISM: Homo sapiens

<400> SEQUENCE: 15

Leu Gln Val Ala Val
1               5

<210> SEQ ID NO 16
<211> LENGTH: 5
<212> TYPE: PRT
<213> ORGANISM: Homo sapiens

<400> SEQUENCE: 16

Gln Val Ala Val Lys
1               5

<210> SEQ ID NO 17
<211> LENGTH: 11
<212> TYPE: PRT
<213> ORGANISM: Homo sapiens

<400> SEQUENCE: 17

Ala Pro Leu Ser Pro Asn Gln Thr Val Glu Ile
1               5                   10

<210> SEQ ID NO 18
<211> LENGTH: 11
<212> TYPE: PRT
<213> ORGANISM: Homo sapiens

<400> SEQUENCE: 18

Gln Thr Val Glu Ile Ser Leu Pro Leu Ser Thr
1               5                   10

<210> SEQ ID NO 19
<211> LENGTH: 11
<212> TYPE: PRT
<213> ORGANISM: Homo sapiens
```

<400> SEQUENCE: 19

Leu Pro Leu Ser Thr Val Gly Ser Val Met Lys
1               5                   10

<210> SEQ ID NO 20
<211> LENGTH: 11
<212> TYPE: PRT
<213> ORGANISM: Homo sapiens

<400> SEQUENCE: 20

Gly Ser Val Met Lys Met Glu Pro Leu Asn Asn
1               5                   10

<210> SEQ ID NO 21
<211> LENGTH: 11
<212> TYPE: PRT
<213> ORGANISM: Homo sapiens

<400> SEQUENCE: 21

Gln Val Ala Val Lys Asn Asn Ile Asp Val Phe
1               5                   10

<210> SEQ ID NO 22
<211> LENGTH: 11
<212> TYPE: PRT
<213> ORGANISM: Homo sapiens

<400> SEQUENCE: 22

Asn Ile Asp Val Phe Tyr Phe Ser Thr Leu Tyr
1               5                   10

<210> SEQ ID NO 23
<211> LENGTH: 11
<212> TYPE: PRT
<213> ORGANISM: Homo sapiens

<400> SEQUENCE: 23

Phe Ser Thr Leu Tyr Pro Leu His Ile Leu Phe
1               5                   10

<210> SEQ ID NO 24
<211> LENGTH: 11
<212> TYPE: PRT
<213> ORGANISM: Homo sapiens

<400> SEQUENCE: 24

Leu His Ile Leu Phe Val Glu Asp Gly Lys Met
1               5                   10

<210> SEQ ID NO 25
<211> LENGTH: 11
<212> TYPE: PRT
<213> ORGANISM: Homo sapiens

<400> SEQUENCE: 25

Glu Asp Gly Lys Met Asp Arg Gln Met Phe Leu
1               5                   10

<210> SEQ ID NO 26
<211> LENGTH: 11
<212> TYPE: PRT
<213> ORGANISM: Homo sapiens

<400> SEQUENCE: 26

```
Arg Gln Met Phe Leu Ala Thr Trp Lys Asp Ile
1               5                   10

<210> SEQ ID NO 27
<211> LENGTH: 11
<212> TYPE: PRT
<213> ORGANISM: Homo sapiens

<400> SEQUENCE: 27

Trp Lys Asp Ile Pro Asn Glu Asn Glu Ala Gln
1               5                   10

<210> SEQ ID NO 28
<211> LENGTH: 5
<212> TYPE: PRT
<213> ORGANISM: Homo sapiens

<400> SEQUENCE: 28

Ser Thr Val Gly Ser
1               5
```

UNITED STATES PATENT AND TRADEMARK OFFICE
CERTIFICATE OF CORRECTION

| | |
|---|---|
| PATENT NO. | : 10,603,265 B2 |
| APPLICATION NO. | : 15/506281 |
| DATED | : March 31, 2020 |
| INVENTOR(S) | : Graca Raposo, Cécile Campagne and Cedric Delevoye |

Page 1 of 1

It is certified that error appears in the above-identified patent and that said Letters Patent is hereby corrected as shown below:

In the Specification

Column 17,
Line 32, "as region" should read --aa region--.
Line 42, "independently g" should read --independently 1µg--.

Signed and Sealed this
Fourth Day of August, 2020

Andrei Iancu
*Director of the United States Patent and Trademark Office*